United States Patent [19]
Richards et al.

[11] Patent Number: 4,969,591
[45] Date of Patent: Nov. 13, 1990

[54] SURGICAL STAPLING SYSTEM

[75] Inventors: William D. Richards, Medway; John C. Meade, Walpole; Ernesto E. Blanco, Belmont, all of Mass.

[73] Assignee: Ophthalmic Ventures, Norwood, Mass.

[21] Appl. No.: 373,622

[22] Filed: Jun. 27, 1989

Related U.S. Application Data

[63] Continuation of Ser. No. 290,865, Dec. 27, 1988, abandoned, which is a continuation of Ser. No. 116,022, Nov. 3, 1987, abandoned.

[51] Int. Cl.⁵ .............................................. A61B 17/00
[52] U.S. Cl. .................................... 227/177; 227/19; 227/132
[58] Field of Search ...................... 227/19, 93, 94, 95, 227/145, 147, 120, 132, 156, 175, 176, 177

[56] References Cited

U.S. PATENT DOCUMENTS

| | | | |
|---|---|---|---|
| 1,568,260 | 1/1926 | Bates | 227/146 X |
| 2,174,708 | 10/1939 | Sears et al. | 227/95 X |
| 2,212,339 | 8/1940 | Cullen | 227/146 |
| 2,520,973 | 9/1950 | Sorenson | 227/93 |
| 2,767,399 | 10/1956 | Widener | 227/146 |
| 3,294,303 | 12/1966 | Anstett | 227/95 |
| 3,604,561 | 9/1971 | Mallina et al. | 206/56 DF |
| 3,646,801 | 3/1972 | Caroli | 227/DIG. 1 |
| 3,949,924 | 4/1976 | Green | 227/DIG. 1 |
| 4,014,492 | 3/1977 | Rothfuss | 227/132 X |
| 4,025,031 | 5/1977 | Chi | 227/132 |
| 4,162,678 | 7/1979 | Fedotov et al. | 227/DIG. 1 |
| 4,196,836 | 4/1980 | Becht | 227/DIG. 1 |
| 4,316,468 | 2/1982 | Klieman et al. | 227/DIG. 1 |
| 4,317,451 | 3/1982 | Cerwin et al. | 227/DIG. 1 |
| 4,410,125 | 10/1983 | Noiles et al. | 227/145 X |
| 4,485,816 | 12/1984 | Krumme | 227/DIG. 1 |
| 4,607,777 | 8/1986 | Ebihara | 227/120 |

Primary Examiner—Paul A. Bell
Attorney, Agent, or Firm—Schiller, Pandiscio & Kusmer

[57] ABSTRACT

A microsurgical stapling system for suturing delicate tissue. The system comprises a staple magazine and a stapler. The magazine has a framework to which a plurality of pre-formed staples are integrally attached in parallel, spaced-apart formation. The stapler comprises a housing, a staple support and ram assembly, a driver body and a driver assembly. The magazine is disposed within the housing and is advanced toward the staple support and ram assembly. The staple support and ram assembly comprises a front wall that engages the front edge of the leading staple in the magazine and a rear wall that engages the trailing edge of the leading staple, whereby the leading staple can be captivated between the front and rear walls. The front wall may not be movable; the rear wall is movable so that it can move down to engage the rear side of a staple which has just passed beneath the rear wall. The staple support and ram assembly also comprises a ram plate slidably mounted between the front and rear walls for driving the leading staple downwardly between the front and rear walls. An ejection slot is formed in the housing through which the leading staple is ejected into the tissue to be sutured. The rear wall and ram plate are coupled to and driven by the driver assembly. The driver assembly retracts the rear wall and ram plate from the inserted staple at the same time the assembly advances the staple magazine toward the front wall.

64 Claims, 11 Drawing Sheets

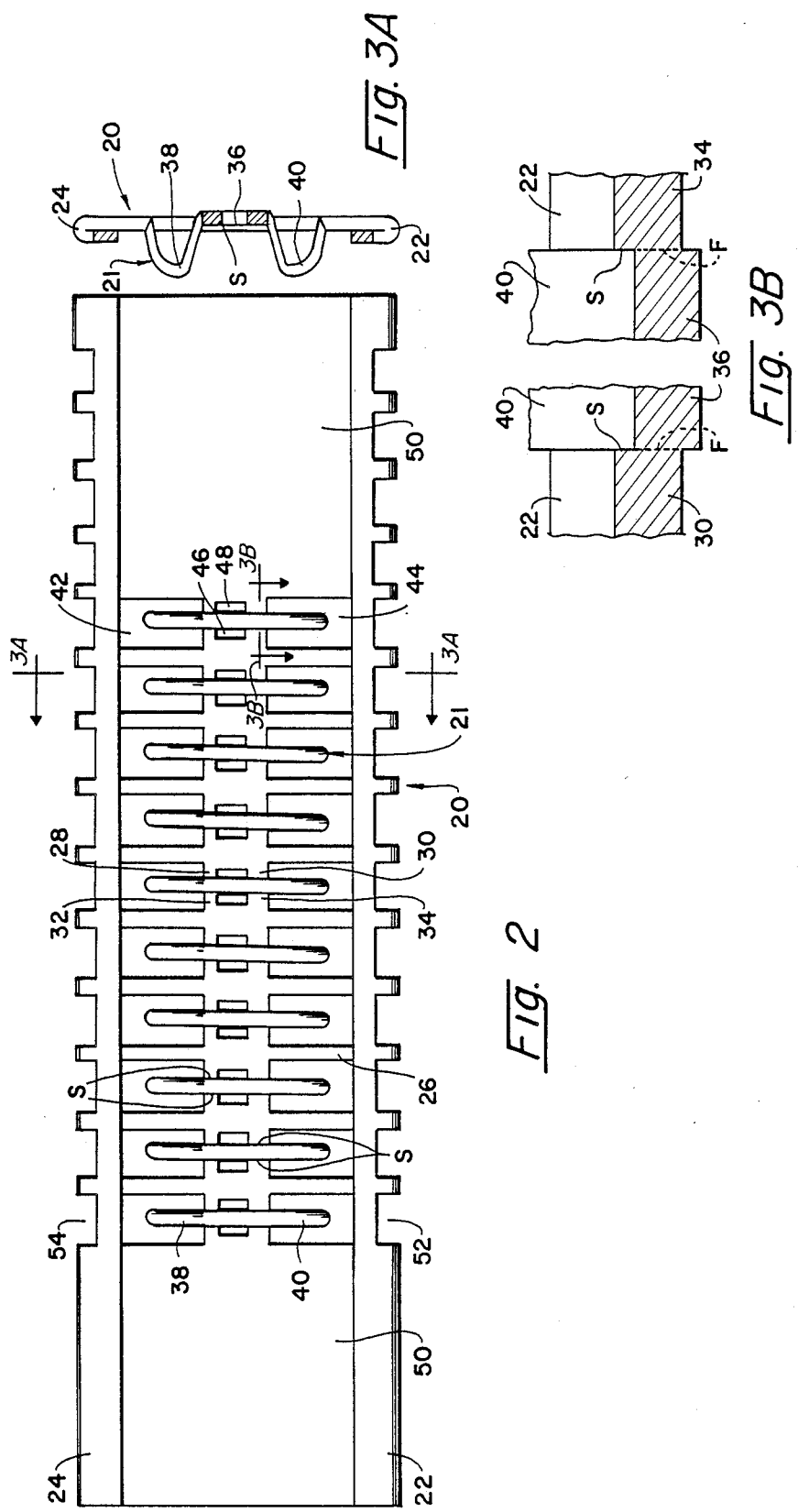

SURGICAL STAPLING SYSTEM

This is a continuation of U.S. patent application Ser. No. 290,865, filed Dec. 27, 1988, and now abandoned, which is a continuation of U.S. patent application Ser. No. 116,022, filed Nov. 3, 1987, and now abandoned.

FIELD OF THE INVENTION

The present invention relates to surgical devices used to suture an incision in human or animal tissue and more particularly to a surgical stapling system for suturing an incision in tissue using miniature staples.

BACKGROUND OF THE INVENTION

Suturing is a very time-consuming phase of most surgical operations. Heretofore it has been realized that suturing time can be reduced considerably by the use of stapling techniques. As a consequence, in recent years several types of stapling systems have come into use for surgical suturing.

By way of example, the following U.S. patents illustrate various types of staplers which have been used for suturing purposes: U.S. Pat. Nos. 3,604,561, 3,646,801, 4,162,678, 4,316,468, 4,317,451 and 4,485,816, and the references cited therein.

However, prior surgical stapling systems suffer from a variety of disadvantages, including but not limited to: (1) excessive size for the intended application; (2) the need to bend the staples across the tissues, which induces severe traumatic effects; (3) the need to extract the stapler anvil from between the staple and the tissue surface after the staples have been implanted; and (4) the inability to maintain precise edge alignment and smoothness between opposing portions of tissue to be sutured, as required in ophthalmic and cosmetic surgery. As a consequence, prior medical staplers have typically been unsuitable for delicate ophthalmic surgical operations where only an absolute minimum of trauma may be induced during the surgical procedure.

OBJECTS OF THE INVENTION

A primary object of the present invention is to provide a stapler for the suturing of incisions in very delicate tissue such as the incisions involved in ophthalmic operations, neurosurgery or plastic surgery.

A more specific object of the invention is to provide a new and improved surgical suturing microstapler system which is characterized by the use of very fine metallic staples made of a stainless steel alloy that is non-injurious to human tissues.

Another specific object of the invention is to provide a microstapler suturing system that is adapted to implant staples with a minimum of trauma, with the implanted staples providing at least the same holding strength as that obtainable with commonly used flexible filament sutures.

Still another object of the invention is to provide a surgical stapling system having pre-shaped staples which are held together in a magazine strip from which they are sheared cleanly after they have penetrated tissue sufficiently so as to hold together the sides of an incision.

Still another object of the invention is to provide a microsurgical stapling system in which the staples are driven with a velocity in excess of the ability of live tissue to react dynamically under the force of the penetrating staples, so as to make it unnecessary to hold together the limp edges of delicate tissue at the time of stapling.

Still another object of the invention is to provide a stapler-type suturing system which is designed to suture together delicate tissue in a manner which reduces trauma to a minimum and assures proper incision alignment, as is essential for ophthalmic or plastic surgery where incision stresses can induce post-operative deformations such as astigmatism or scarring.

A further object of the invention is to provide a stapling system having staples which are shaped as close as possible to the atraumatic curvature best suited to reduce tissue pull and tear during penetration.

Still another object of the invention is to provide a microsurgical stapling system which does not require the use of a staple-bending anvil that must be retracted after the staple is implanted.

SUMMARY OF THE INVENTION

These and other objects are achieved by a surgical stapling system comprising a disposable magazine of preformed staples and a stapler for driving the leading one of said staples into human or animal tissue adjacent an incision so as to suture the incision. The disposable staple magazine comprises a grid-like framework for supporting the preformed staples in parallel, spaced-apart formation. Each staple has two legs with pointed ends that are adapted to pierce the tissue to be sutured. The stapler comprises (1) a housing having a staple ejection slot and a surface for supporting the staple magazine, (2) a staple support assembly secured to the housing for supporting front and rear surfaces of the leading staple in the magazine, (3) a ram slidably mounted to the staple support assembly for driving the leading staple out of the staple magazine and into the tissue to be sutured, and (4) a driver assembly for advancing the staple magazine and for causing the ram to move so as to enable the ram to drive the leading staple into the tissue to be sutured.

BRIEF DESCRIPTION OF THE DRAWINGS

For a fuller understanding of the nature and objects of the present invention, reference should be had to the following detailed description of the invention, which is to be read together with the accompanying drawings wherein:

FIG. 2 is a plan view of the staple magazine;

FIGS. 3A and 3B are cross-sectional views of the staple magazine taken along lines 3A-3A and 3B-3B of FIG. 2, respectively.

DETAILED DESCRIPTION OF THE INVENTION

Figure 1:
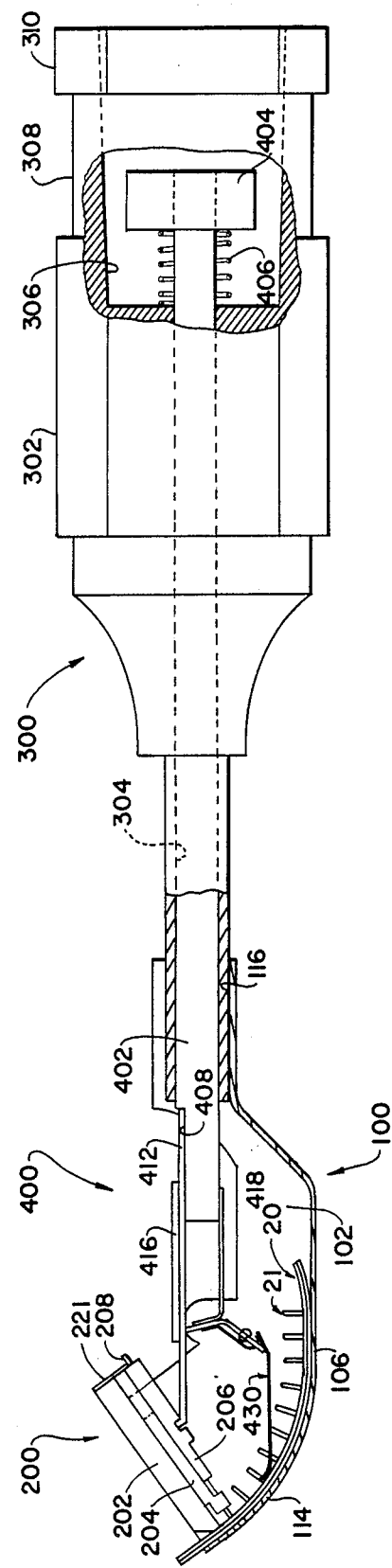
FIG. 1 is a side elevation view, partly in cross-section, and partly broken away, of the stapler and staple magazine of the present invention.

Referring first to FIG. 1, the surgical stapling system of the present invention comprises a staple magazine 20 and a stapler for dispensing the staples secured to the magazine. The stapler comprises a housing 100, a staple support and ram assembly 200, a driver body 300 and a driver assembly 400.

As illustrated in FIGS. 1, 2 and 3A, staple magazine 20 is formed from a flat sheet of material that is non-reactive with human or animal tissue, such as stainless steel sheet metal. Magazine 20 comprises a grid-like framework to which a plurality of staples 21 are attached in parallel, spaced-apart fashion. Staples 21, and the integral framework to which they are attached, are formed in a suitable manner, e.g. by die punching and forming. As illustrated in FIGS. 2 and 3A, the grid-like framework of staple magazine 20 comprises side frame members 22 and 24, between which staples 21 are disposed, and cross frame members 26. Side frame members 22 and 24 are folded inwardly so as to contact cross frame members 26 adjacent the point of connection of the side frame members to the cross frame members. On account of such folding, the outermost portions of staple magazine 20 are twice as thick as the intermediate portion of the magazine (see FIG. 3A). Each cross frame member 26 has two tiny tabs 28 and 30 on one side joining a staple 21 to the cross frame member 26, and two tiny tabs 32 and 34 are secured to the opposite side of the staple joining the staple to the adjacent cross frame member 26. The width of magazine 20 is slightly less than the spacing between the sidewalls of housing 100, the sidewalls and spacing therebetween being described in greater detail below.

To facilitate proper separation of the staples from magazine 20, tabs 28, 30, 32 and 34 are preweakened (i.e., they are presheared or prestressed or scored or otherwise weakened in some way) so as to reduce the amount of shearing force required to separate the staples from the tabs and to define the point of separation of the staples from the tabs, thereby facilitating deployment of the staples and avoiding a risk of premature deformation of the staples when they are impacted by staple support and ram assembly 200, as will hereinafter be described in further detail. Preferably, this preweakened condition is achieved by prestressing the contact points between tabs 28, 30, 32 and 34 and the staple's body 36 with suitable tooling at the time of manufacture, whereby body 36 of the staple will be forced downward slightly relative to tabs 28, 30, 32 and 34 so as to create a microscopic step S and fracture lines F between the staple and the tabs (see FIGS. 2, 3A and 3B). The effect of this prestressing is such that when the staple is thereafter impacted by staple support and ram assembly 200, tabs 28, 30, 32 and 34 are quickly and easily sheared off at step S and fracture lines F, due to the prestressing of the tabs at their separation point. In practice, it has been found that microscopic step S should be formed so as to have a height of approximately 25—50% of the thickness of staple body 36 to obtain superior results.

Staples 21 are formed with a body or spine portion 36 (see FIG. 3A) and two convexly curved legs 38 and 40 that project above the plane of staple magazine 20. The legs of staples 21 are formed so that they diverge slightly from one another, e.g. each leg extends at an angle of approximately 15°-20° degrees to the vertical (see FIG. 3A).

Openings 42, 44, 46 and 48 define the configuration of the framework of magazine 20. Additionally, each staple magazine has leading and trailing end solid cross members 50 that have a greater width than the cross frame members 26. Cross members 50 are provided to assist in supporting the first and last staples in the magazine. By folding side frame members 22 and 24 inwardly onto cross frame members 26, side pockets 52 and 54 are formed at the outer edges of magazine 20. Side pockets 52 and 54 give a "railroad track" effect to the outer edges of magazine 20.

The stapling system illustrated in FIG. 1 is preferably a disposable system that is discarded after all of the staples 21 in the magazine 20 have been dispensed. As such, magazine 20 is inserted in housing 100 during fabrication of the stapler. Skilled practitioners will readily appreciate, however, that the stapling system could easily be made reusable by providing a staple magazine reloading slot (not shown) in housing 100.

Since the stapling system of the present invention is intended for delicate surgeries, the system is of microsurgical dimensions. Specifically, the overall length of the stapler apparatus shown in FIG. 1 is approximately 10 mm, and the width of a staple 21, i.e. the distance between the end points of a staple before insertion, is about 0.05 mm.

Figure 4:
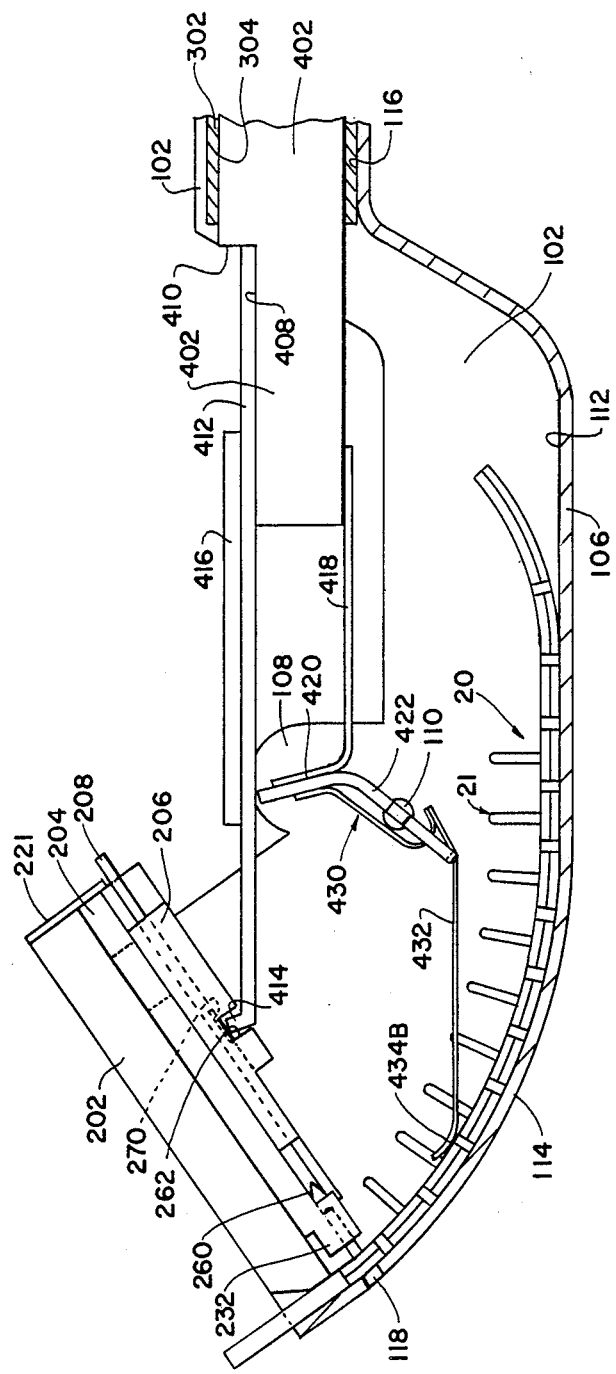
FIG. 4 is an enlarged, cross-sectional, side elevation view of the forward portion of the surgical stapler and of the entire staple magazine illustrated in FIG. 1.
Figure 8:
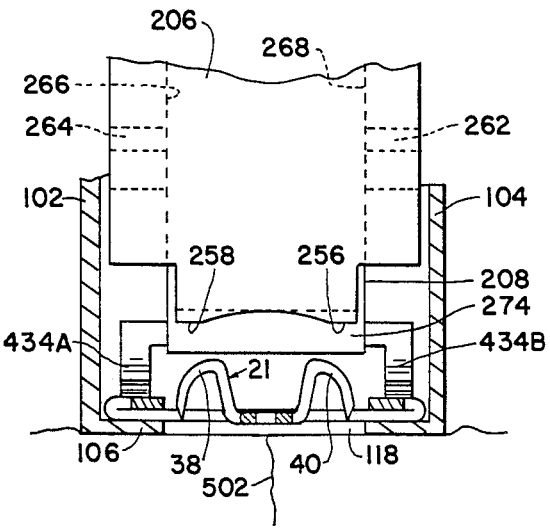
FIGS. 8, 10 and 12 are partial, cross-sectional front elevation views of the present invention taken along line 8—8 in FIG. 7, line 10—10 of FIG. 9 and line 12—12 in FIG. 11, respectively, illustrating the operation of the present invention at three different stages of operation, with the operational stages shown in FIGS. 8, 10 and 12 corresponding respectively to the operational stages shown in FIGS. 7, 9 and 11. Portions of the magazine positioner feet have been removed in FIGS. 8, 10 and 12 to facilitate description of the present invention.
Figure 9:
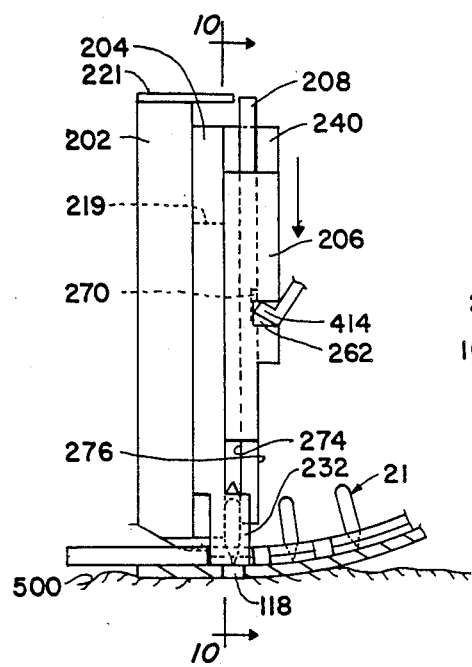

Turning now to FIGS. 1, 4 and 8, stapler housing 100 comprises a three-sided body comprising identical, opposing sidewalls 102 and 104 (see FIG. 8) and bottom wall 106. Sidewall 102 includes an upstanding, curved portion 108 (FIG. 4). A correspondingly shaped curved portion (not shown) is formed in sidewall 104 opposite curved portion 108. Hole 110 is formed in sidewall 102 below curved portion 108 and is positioned a selected distance above bottom wall 106, as described more fully hereinafter. An identically sized and placed hole (not shown) is formed in sidewall 104 opposite hole 110.

Bottom wall 106 is secured to sidewalls 102 and 104 along the bottom edge of the sidewalls. The width of bottom wall 106 is selected so that sidewalls 102 and 104 are spaced apart from one another a distance such that magazine 20, staple support and ram assembly 200, driver body 300 and driver assembly 400 may be received between the sidewalls, as described in greater detail below. More specifically, the width of bottom wall 106 is slightly greater than the width of staple magazine 20, whereby sidewalls 102 and 104 can act as guide surfaces for the magazine, as discussed below. Bottom wall 106 comprises an inner surface 112 for supporting staple magazine 20 (FIG. 4). Portion 114 of bottom wall 106 curves upwardly toward the front end of housing 100. A driver body support surface 116 (FIG. 4) is provided on the inner surface of bottom wall 106 adjacent the rear end of housing 100. Ejection slot 118 is formed in curved portion 114 adjacent the front end of housing 100.

Figure 10:
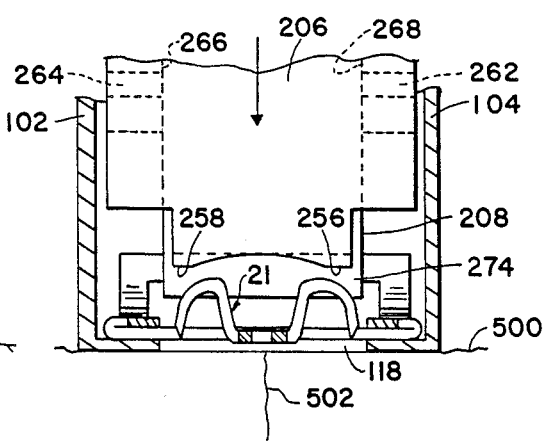
Figure 12:
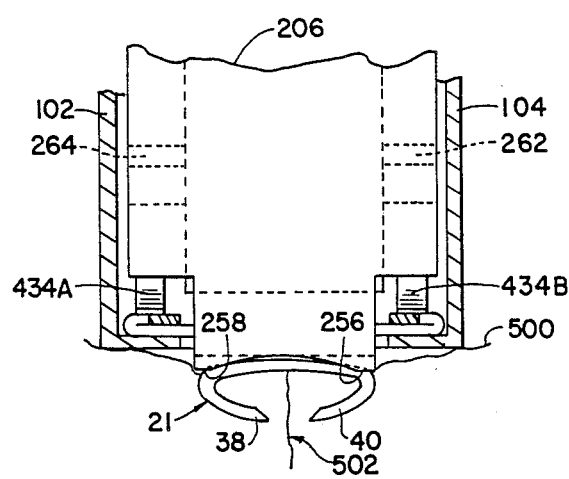

Bottom wall 106 may be formed integrally with sidewalls 102 and 104 or it may be secured thereto by a suitable process, e.g. welding. Preferably, sidewalls 102 and 104 and bottom wall 106 are made from a single piece of stainless-steel sheet metal cut and formed so as to form housing 100, as indicated in FIGS. 8, 10 and 12. Alternatively, housing 100 may be formed from other materials and by other processes, the only requirement being that the material must be substantially non-reactive with human and animal tissue and fluids and that the material must be sufficiently rigid for the stapler to function as described hereinafter.

Figure 5:
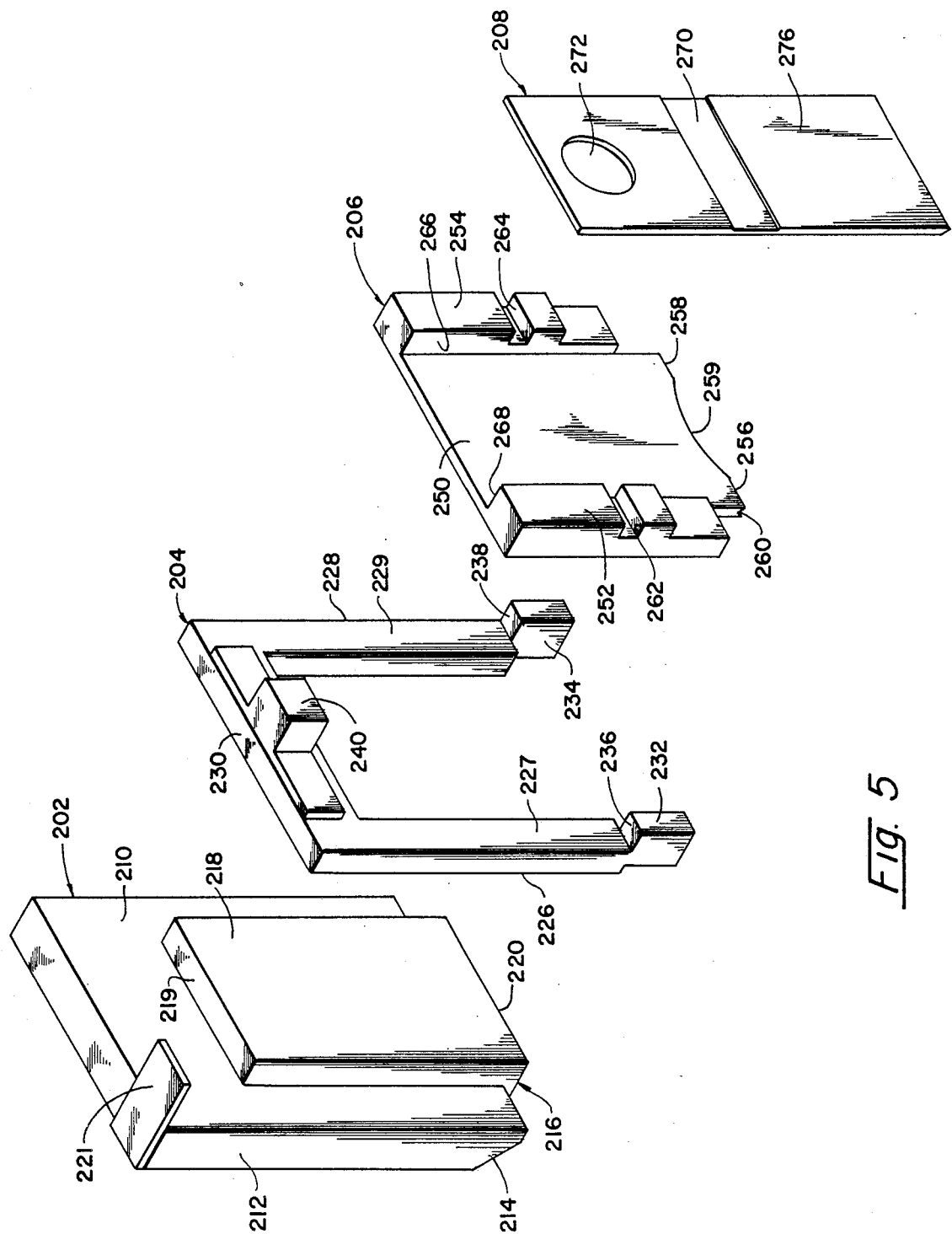
FIG. 5 is an enlarged, exploded, isometric view of the ram and staple support assembly of the present invention.

Referring next to FIGS. 4, 5 and 8, staple support and ram assembly 200 comprises bulkhead 202, staple magazine positioner 204, ram 206 and guide plate 208.

Bulkhead 202 comprises inner surface 210 and opposing side edges, one of which is visible in FIG. 5 and is identified as 212. The bottom edge 214 of bulkhead 202 tapers upwardly away from inner surface 112 of bottom wall 106 of stapler housing 100. Block 216 is attached to and protrudes from inner surface 210 a selected distance that corresponds to the thickness of magazine positioner 204, as described in greater detail below. The width and height of block 216 are selected so that the block, in combination with inner surface 210, acts as a guide and a stop for magazine positioner 204, as described hereinafter. Block 216 comprises sliding surface 218 that extends in parallel with inner surface 210 and surface 219 that extends perpendicularly to inner surface 210. Bottom edge 220 of block 216 extends slightly below the bottom-most portion of bottom edge 214 of bulkhead 202. A stop 221 is attached to the top of bulkhead 202.

Staple magazine positioner 204 comprises legs 226 and 228 which are connected together at their top ends by cross piece 230. Legs 226 and 228 comprise front surfaces 227 and 229, respectively, and are spaced apart a distance that is substantially equal to the width of block 216 so that the block can function as a guide for positioner 204, as described hereinafter. The thickness of legs 226 and 228 is substantially equal to the distance block 216 protrudes from inner surface 210 of bulkhead 202. Feet 232 and 234 are attached to the bottom ends of legs 226 and 228, respectively. Ram stop surfaces 236 and 238 are provided on top of feet 232 and 234, respectively. The length and width of feet 232 and 234 are substantially equal to the length and width of side pockets 52 and 54 of staple magazine 20 (FIG. 2), and feet 232 and 234 extend outwardly from legs 226 and 228, respectively, so that the feet 232 and 234 may be inserted into the side pockets 52 and 54 of staple magazine 20, as discussed below. Stud 240 is secured to cross piece 230 intermediate the length of the cross piece and extends outwardly from the cross piece a selected distance.

Ram 206 comprises ram plate 250 and side members 252 and 254 attached to the sides of the ram plate. Lugs 256 and 258 are provided at the bottom end of ram plate 250 and are spaced apart from one another a distance equal to the spacing between legs 38 and 40 of staple 21 (see FIG. 3A). Convexly curved portion 259 is disposed between lugs 256 and 258 at the bottom end of ram plate 250. The radius of curvature of curved portion 259 is approximately equal to the radius of curvature of the back or spine of a fully inserted staple, as described hereinafter. A staple-engaging groove 260 (FIG. 5) is formed in the bottom of ram plate 250. Notches 262 and 264 are formed in side members 252 and 254, respectively, so as to lie along a common plane. Side members 252 and 254 are spaced apart from one another a distance substantially equal to the spacing between feet 232 and 234 of staple magazine positioner 204. Side members 252 and 254 comprise inner surfaces 266 and 268 (FIGS. 5 and 8).

Guide plate 208 is a flat plate having a shallow groove 270 formed therein adjacent the middle of the plate. An aperture 272 sized to receive stud 240 of staple magazine positioner 204 is positioned adjacent the top end of guide plate 208 such that the distance between the top edge of groove 270 and the bottom edge of aperture 272 is equal to or greater than the distance between the top edge of ram 206 and the top edges of notches 262 and 264. The width of guide plate 208 is slightly less than the distance between inner edges 266 and 268 (FIG. 8) of ram 206. Guide plate 208 has a front surface 274 (FIG. 8) and a rear surface 276 (FIG. 5).

Bulkhead 202, magazine positioner 204, ram 206 and guide plate 208 are mounted at the front end of housing 100 in cooperative relationship with one another. Bulkhead 202 is secured to housing 100 so that a magazine ejection slot 280 (FIG. 7) is formed between bottom wall 106 of housing 100 and bottom edges 214 and 220 of bulkhead 202. Magazine ejection slot 280 is sized to allow the framework of magazine 20, including side frame members 22 and 24 (see FIG. 2) to pass through the slot and to prevent staples 21 secured to the magazine framework from passing through the slot. The side edges of bulkhead 202 are secured to the sidewalls 102 and 104 of housing 100 adjacent the front end of the housing so that sliding surface 218 of bulkhead 202 is positioned just forward of housing ejection slot 118 (FIG. 7) and so that sliding surface 218 extends substantially perpendicularly to that portion of housing inner surface 112 (FIG. 4) located adjacent ejection slot 118.

Magazine positioner 204 is positioned against bulkhead 202 so as to slidingly engage the bulkhead's inner surface 210. Legs 226 and 228 straddle and are slidingly guided by block 216. Since, as described above, block 216 extends perpendicularly to inner surface 210 for a distance equal to the thickness of positioner legs 226 and 228, sliding surface 218 of bulkhead 202 is coplanar with the front surfaces 227 and 229 of the legs of the magazine positioner when magazine positioner 204 is positioned against bulkhead 202 in the foregoing manner. Downward travel of magazine positioner 204 is stopped when its feet 232 and 234 engage bottom wall 106 of housing 100.

Ram 206 is positioned to slidingly engage the planar surface consisting of the bulkhead's sliding surface 218 and the magazine positioner's front surfaces 227 and 229. Ram 206 is positioned beneath stud 240 with the result that the stud limits the upward travel of the ram. The downward travel of the ram is limited by the engagement of the bottom surfaces of ram side members 252 and 254 with ram stop surfaces 236 and 238, respectively, of magazine positioner 204.

Guide plate 208 is positioned to slidingly engage ram plate 250. The inner surfaces 266 and 268 of ram 206 flank guide plate 208 and thereby guide the path of travel of the guide plate. Stud 240 of magazine positioner 204 extends through aperture 272 of guide plate 208 whereby (a) ram grooves 262 and 264 are substantially aligned with the guide plate's shallow groove 270 when ram 206 engages the magazine positioner's stud 240, and (b) guide plate 208 is coupled to move with magazine positioner 204. By this arrangement of the elements of the staple support and ram assembly 200, ram lugs 256 and 258 are positioned directly above housing ejection slot 118 and the bulkhead's sliding surface 218 is spaced from front surface 274 (FIG. 8) of guide plate 208 a distance approximately equal to the thickness of a staple 21. As such, the bulkhead's sliding surface 218 is positioned directly above the forward edge of ejection slot 118 and the guide plate's front surface 274 is positioned directly above the trailing edge of ejection slot 118.

Referring next to FIGS. 1 and 4, driver body 300 comprises hollow socket-like member 302 having an axially extending bore 304 which is counterbored as shown at 306. The exterior of member 302 has a reduced diameter portion 308, resulting in a flange 310. The forward end of member 302 is welded or otherwise attached to driver body support surface 116 and to adjacent portions of sidewalls 102 and 104. The rear end of driver body 300, including counterbore 306, reduced diameter portion 308 and flange 310, is adapted for attachment to a stapler driver of the type disclosed in Richards et al., U.S. patent application Ser. No. 906,151 filed Sept. 11, 1986 which is incorporated herein by reference.

Referring now to FIGS. 1, 2 and 4, driver assembly 400 comprises shaft 402 slidably disposed in bore 304. Flange 404 (FIG. 1) is attached to the rear end of shaft 402 and is sized so that a gap exists between counterbore 306 and flange 404 so as to allow the flange to move axially in counterbore 306 without contacting the sidewalls of the latter. A coil spring 406 surrounds shaft 402 and is captivated between flange 404 and the base of counterbore 306. The forward end of shaft 402 has a flat portion 408 (FIG. 4) that terminates at shoulder 410. The rear end of ram driver plate 412 rests in flat portion 408 and is secured to shaft 402 adjacent shoulder 410, e.g. by spot welding. It is to be appreciated that driver plate 412 is attached to shaft 402 only near shoulder 410, so that the majority of the back end of driver plate 412 only rests on and is not secured to flat 408 of shaft 402. Ram driver plate 412 has an upstanding tab 414 (FIG. 4) at its front end. As described more fully hereinafter, tab 414 is sized to be received simultaneously in notches 262 and 264 of ram 206 and shallow groove 270 of guide plate 208 (see FIG. 5). Ram driver plate 412 is made from a relatively flexible material, such as, for example, 28 gauge stainless-steel sheet metal. A rigid stiffener plate 416 is secured to ram driver plate 412 adjacent the middle of the latter so that ram driver plate 412 is rendered inflexible along the length of its contact with stiffener plate 416.

Spring plate 418 (FIGS. 1 and 4) contacts the forward end of shaft 402 (FIG. 4) in diametrically opposed relation to ram driver plate 412. Spring plate 418 is made from a relatively resilient material, such as, for example, 28 gauge stainless-steel sheet metal.

Spring plate 418 comprises a foot 420 (FIG. 4) to which the upper half of rocker plate 422 is attached. The lower half of rocker plate 422 (FIG. 4) is pivotally mounted to housing sidewalls 102 and 104 by a pair of opposing tabs or trunnions (not shown) that extend into hole 110 in sidewall 102 and its opposing counterpart (not shown) in sidewall 104. Rocker plate 422 is a flat plate, preferably made from stainless-steel sheet metal, which is bent so as to subtend an arc of approximately 135 degrees.

Referring now to FIGS. 1, 4 and 8, a pawl 430 is attached to the upper half of rocker plate 422. The pawl comprises a foot 432 that extends forwardly and downwardly from rocker plate 422. Pawl 430 is configured and hole 110 and its opposing counterpart (not shown) are positioned relative to housing bottom wall 106 so that the pawl contacts staple magazine 20. Foot 432 is bifurcated at its lower end so as to form feet 434A and 434B (FIG. 8). The latter are sized and curved so as to engage and extend into magazine side pockets 52 and 54, respectively, when positioned directly above the side pockets. Foot 432 is configured so that successive ones of staples 21 may be fed through the foot and between feet 434A and 434B. Pawl 430 is made from a relatively flexible material, such as, for example, 32 gauge stainless-steel sheet metal.

Figure 7:
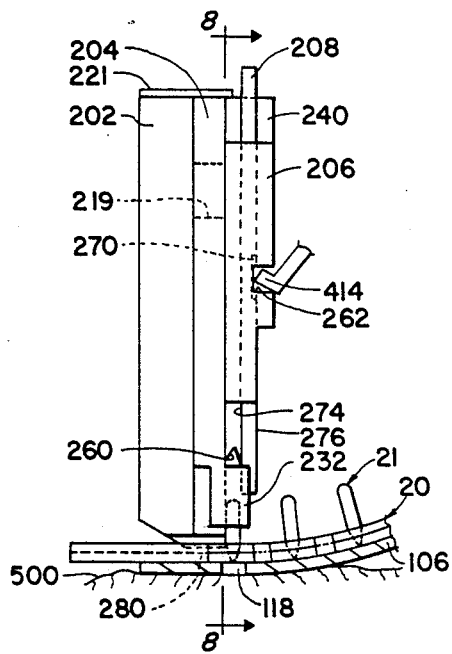
FIGS. 7, 9 and 11 are partial, cross-sectional, side elevation views of the present invention illustrating the operation of the present invention at three different stages of operation.

During the fabrication of the stapling system of the present invention, staple magazine 20 is inserted in housing 100 so that the cross piece 50 which is adjacent to the leading staple in the magazine extends forwardly of bulkhead 202 and through magazine ejection slot 280 (FIG. 7). In this position, the leading staple in the magazine contacts sliding surface 218 (FIG. 5) of bulkhead 202 which, as noted above, is aligned with the forward edge of housing ejection slot 118. Consequently, the leading staple in the magazine is positioned directly above ejection slot 118.

By forming magazine 20 so that its width is only slightly less than the spacing between housing sidewalls 102 and 104, as noted above, the staple magazine, including staples 21, is centered laterally above ejection slot 118. Also, when the leading staple engages sliding surface 218 of bulkhead 202, ram lugs 256 and 258 are positioned directly above the leading staple, and the front surface 274 of guide plate 208 (FIG. 8) is positioned directly above the trailing edge of the leading staple. Additionally, feet 232 and 234 of magazine positioner 204 are positioned directly above magazine side pockets 52 and 54, respectively, when the leading staple engages sliding surface 218 of bulkhead 202.

Operation of the surgical stapling system will now be described. Referring to FIG. 1, to use the stapling system illustrated in FIG. 1, driver body 300 is secured to a stapling system driver of the type disclosed in the aforementioned Richards et al. U.S. patent application Ser. No. 906,151 filed Sept. 11, 1986. To facilitate attachment of the driver to driver body 300, counterbore 306 is sized to receive and frictionally engage the front extension of the Richards et al. driver, and reduced diameter portion 308 and flange 310 are sized to receive and engage the clasp member of the Richards et al. driver. When driver body 300 is secured to the Richards et al. driver, the striker member of the latter is aligned to engage and drive flange 404, and shaft 402 attached thereto, against the bias of spring 406, toward the front of the stapling system. As such, driver body 300 is attachable to the Richards et al. driver in substantially the same manner in which the stapling system disclosed in the Richards et al. patent application is attached to the driver disclosed therein.

Turning now to FIGS. 4–12, curved portion 114 of housing 100 is positioned to contact the surface of tissue 500 so that ejection slot 118 straddles the incision 502 to be sutured, as illustrated in FIGS. 7 and 8. Curved housing portion 114 is provided so that no sharp edges are brought into contact with the tissue to be sutured; in addition, the curvature provided to the housing facilitates presentation of the stapler to the tissue while keeping the aforementioned Richards et al. driver elevated from the tissue for easier grasping by the surgeon. This arrangement also provides a superior field of view for the surgeon during operation of the device. Next, the Richards et al. driver to which the stapling system is attached is actuated, causing the striker member of the driver to contact and drive flange 404 (FIG. 1), and shaft 402 attached thereto, forward against the bias of spring 406. The forward movement of shaft 402 is transmitted to ram driver plate 412 since the plate is secured to the shaft.

Figure 6:
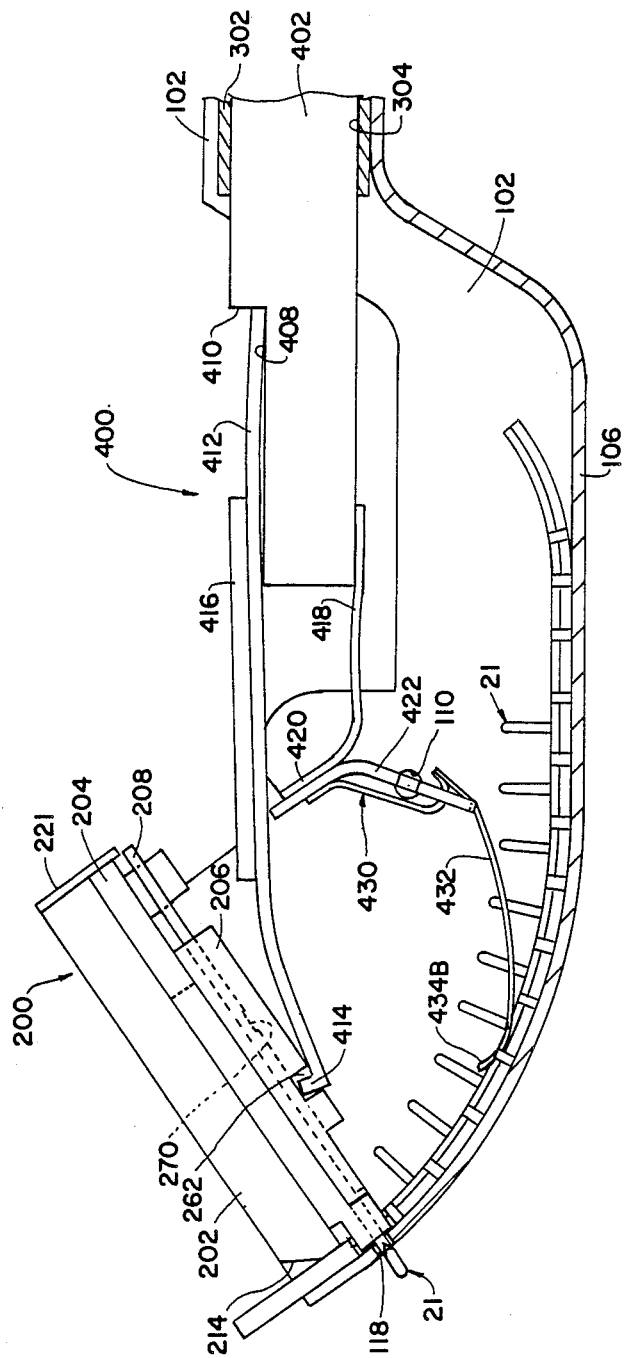
FIG. 6 is a view similar to that of FIG. 4, except that elements of the stapler are shown in the positions the at the instant that the ejected staple is fully inserted into the tissue to be sutured.

As ram driver plate 412 is driven forwardly, the driver plate's upstanding tab 414 is urged against the bottom edge of ram notches 262 and 264 (FIG. 5) and guide plate shallow groove 270 whereby the drive force of driver plate 412 is transmitted to ram 206 and guide plate 208. Ram driver plate 412 is made from a relatively flexible material so that forward movement of shaft 402 is translated downwardly so as to drive ram 206 and guide plate 208 downwardly toward the leading staple. As illustrated in FIG. 6, stiffener plate 416 prevents the middle portion of ram driver plate 412 from deflecting during this driving motion, whereby the forward portion of the ram driver plate 412 is deflected sufficiently to cause its upstanding tab 414 to move downwardly along an imaginary plane that extends substantially parallel to sliding surface 218 of bulkhead 202. Since ram driver plate 412 is attached to flat portion 408 of shaft 402 only adjacent to the shoulder 410, when the ram driver plate 412 is deflected downwardly as illustrated in FIG. 6, a small amount of deflection will occur in the rear portion of the ram driver plate as well. This deflection of the rear portion of the ram driver plate increases the total deflection of the forward portion of the ram driver plate thereby ensuring that tab 414 moves in parallel with sliding surface 218 of bulkhead 202.

By forming stud 240 of staple magazine positioner 204 so that it extends through aperture 272 in guide plate 208, magazine positioner 204 is coupled to move with guide plate 208. By this arrangement, magazine positioner 204 and guide plate 208 are driven downwardly together by ram driver plate 412 toward the leading staple, so that the magazine positioner's feet 232 and 234 enter magazine side pockets 52 and 54, respectively, adjacent the leading staple. Magazine positioner 204 is driven downwardly by ram driver plate 412 until its feet 232 and 234 contact housing bottom surface 106.

As magazine positioner 204 is driven towards housing bottom surface 106, it forces the staple magazine downward so that the body 36 of the staple (projecting below the tabs 28, 30, 32 and 34 due to the prestressing described above) will enter the ejection slot 118 in housing 100, providing added stability to the staple being driven and bringing the body 36 of the staple closer to and hence more flush with tissue 500.

Figure 11:
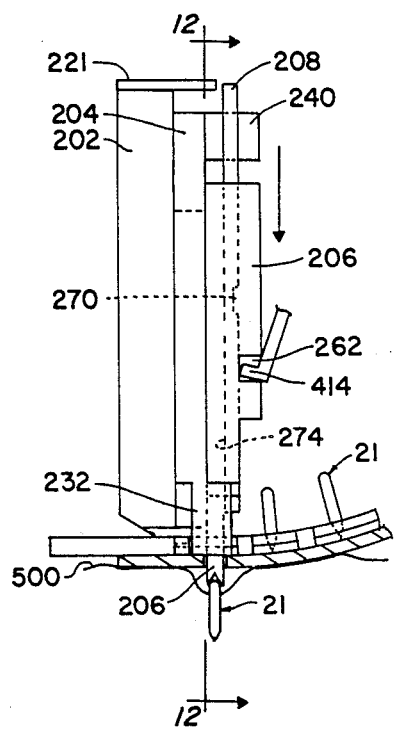

As guide plate 208 is driven downwardly, its front surface 274 (FIG. 9) engages and slides along the trailing edge of the leading staple until the magazine positioner's feet 232 and 234 engage bottom wall 106 of housing 100, as illustrated in FIGS. 11 and 12. By inserting the magazine positioner's feet 232 and 234 in magazine side pockets 52 and 54, respectively, magazine 20 is prevented from moving along its length or from side to side. By causing front surface 274 of guide plate 208 to engage the trailing edge of the leading staple, the staple, as well as ram plate 250, is captivated between the bulkhead's sliding surface 218 and the guide plate's front surface 274. By this captivation, a staple insertion path is created for the leading staple that extends substantially perpendicularly to that portion of housing bottom wall 106 which is adjacent to ejection slot 118.

After the magazine positioner's feet 232 and 234 contact bottom wall 106, continued downward movement of ram driver plate 412 causes its tab 414 to slip out of the guide plate's shallow groove 270, as illustrated in FIG. 11. As a result of this decoupling of magazine positioner 204 and guide plate 208 from ram driver plate 412, further downward movement of plate 412 is transmitted only to ram 206.

As ram 206 continues its downward travel, its lugs 256 and 258 engage the top edge of staple legs 40 and 38, respectively, of the leading staple. When ram lugs 256 and 258 engage the leading staple, a small portion of the top edge of staple legs 38 and 40 enters ram notch 260. Notch 260 is provided so that ram plate 250 remains engaged with the leading staple during the staple insertion process. Further downward movement of ram plate 250 drives legs 38 and 40 of the leading staple through housing ejection slot 118 and into tissue 500 on opposite sides of incision 502. By forming each leg so that it initially extends at an angle of approximately 15°–20° degrees to the vertical, the legs will enter the tissue along curved paths. As the legs penetrate the tissue along these curved paths, the tissue adjacent to incision 502 will be drawn together. Curved portion 259 of ram 206 is provided so that the downward force of ram plate 250 is transmitted to the legs of the leading staple, and not to the bridge of the staple, so as to cause the staple legs to enter the tissue along the aforementioned curved paths.

At a point in the downward travel of ram plate 250, the downward force acting on the leading staple will exceed the shear strength of magazine tabs 28, 30, 32 and 34. At this point, the leading staple will be sheared off of magazine 20 at the tab's fracture lines F (see FIG. 3B) and further inserted into the tissue to be sutured. It is to be appreciated that the leading staple is initially captivated between and is guided by the bulkhead's sliding surface 218 and the guide plate's front surface 274; after the staple passes beyond the bottom edges of bulkhead 202 and guide plate 208, it is guided by the groove 260 formed on the bottom of ram 206 until the staple is sheared from the magazine.

Just after the leading staple is fully inserted into the tissue, as illustrated in FIG. 12, the bottom surfaces of the ram's side members 252 and 254 will contact ram stop surfaces 236 and 238. At this juncture, further downward movement of ram 206 and ram driver plate 412 is prohibited and the staple insertion process is completed.

Referring now especially to FIGS. 4 and 6, as ram river plate 412 is driven forwardly and downwardly, the rocker plate 422 is urged to rotate in a counterclockwise direction about hole 110. As noted above, rocker plate 422 has trunnions (not shown) that extend into hole 110 and the opposing hole (not shown) formed in sidewall 104 that allow this pivotal movement of the rocker plate to occur. Upstanding curved portions 108 of the housing prevent the upper half of rocker plate 422 from moving laterally during its pivotal movement.

As rocker plate 422 is pivoted forwardly, pawl 430, by virtue of its attachment to the rocker plate, is also caused to pivot in a counterclockwise direction about hole 110. This counterclockwise rotation causes pawl foot 432 to slide rearwardly along magazine 20, away from bulkhead 202. The configuration of pawl 430 is selected so that when ram side members 252 and 254 (FIG. 5) engage ram stop surfaces 236 and 238 (FIG. 5), respectively, pawl feet 434A and 434B are positioned directly above those magazine pockets 54 and 52 positioned several side pockets behind the side pockets adjacent the leading staple (see FIGS. 4 and 6). The width and curvature of pawl feet 434A and 434B are selected so that under the bias of pawl 430, the feet will extend a selected distance into side pockets 54 and 52, respectively, when positioned directly above those side pockets.

After the leading staple has been fully inserted into the tissue to be sutured, the striker mechanism of the Richards et al. driver is disengaged from shaft 402, thereby allowing coil spring 406 to urge flange 404, and shaft 402 attached thereto, away from bulkhead 202. As shaft 402 moves away from bulkhead 202, tab 414 of ram driver plate 412 pulls ram 206 upwardly, along the bulkhead's sliding surface 218 and the magazine positioner's front surfaces 227 and 229, away from ejection slot 118.

While magazine positioner 204 and guide plate 208 are not directly coupled to ram 206, when ram 206 is first pulled away from ejection slot 118 by ram driver plate 412, magazine positioner 204 and guide plate 208 will nonetheless start to move upwardly along with the ram due to the frictional contact between the withdrawing tab 414 of ram driver plate 412 and the rear surface 276 of guide plate 208. Magazine positioner 204 and guide plate 208 are dragged upward with the retreating tab 414 of ram driver plate 412 (and also ram 206, of course) until the cross piece 230 of magazine positioner 204 engages stop 221 which is fixed to the top of bulkhead 202, whereupon upward movement of magazine positioner 204 and guide plate 208 ceases. Tab 414 of ram driver plate 412 continues to move upward, however, sliding along the rear surface 276 of guide plate 208 and carrying ram 206 with it, until the top of the ram also engages stop 221, whereupon tab 414 reengages surface groove 270 of guide plate 208 and magazine positioner 204, ram 206 and guide plate 208 have all been moved back to their starting positions, as illustrated in FIGS. 1 and 4.

As shaft 402 is urged rearwardly away from bulkhead 202, rocker plate 422 is urged to rotate in a clockwise direction about hole 110. Pawl 430 rotates with rocker plate 422 driving foot 432 forward. Pawl feet 434A and 434B extend into magazine pockets 54 and 52, respectively, a distance sufficient to ensure that forward movement of foot 432 will be transmitted to magazine 20. The length and configuration of pawl 430 is selected so that when ram 206 has been driven back to its aforementioned starting position illustrated in FIGS. 1 and 4, the pawl will have driven the next staple in the staple magazine into engagement with sliding surface 218 of bulkhead 202. As this indexing of the magazine occurs, the portion of the magazine to which the leading staple was attached is driven forwardly, out of the housing between bottom wall 106 and the bulkhead's bottom edges 214 and 220. Surface 220 of block 216 extends below the top surface of magazine side members 22 and 24 into the gap formed between the side members, so as to guide the magazine through ejection slot 280 (as well as to provide a better surface for the lead staple to rest against). The second staple thus becomes the leading staple and the foregoing staple insertion process may be repeated for the new leading staple. After all of the staples in the magazine have been ejected, the entire stapling system is discarded.

As noted above, the stapling system of the present invention is sized for use in microsurgical operations. Of course, it should be appreciated that the size of the stapling system may be modified to suit the requirements of the surgical procedure in which the stapling system is to be used.

Sliding surface 218 of bulkhead 202 and guide plate front surface 274 together slidingly support the front and rear surfaces, respectively, of the leading staple during the majority of the staple insertion process. As a result of this support, the ejected staple enters the tissue to be sutured along a known and substantially "wobble-free" path. This controlled insertion of the staple is especially advantageous in ophthalmic, cosmetic and other delicate surgeries where smooth and accurate insertion of the staple is essential if one is to achieve even suturing and to minimize scarring of the sutured tissue.

Another advantage of the present stapling system is that staples are inserted without the use of an anvil. In known prior art devices, an anvil must be removed from between the tissue and the fully inserted staple to complete the staple insertion process. This anvil removal often introduces pulling, abrasion and other trauma to the sutured tissue.

It is anticipated that certain changes may be made to the surgical stapling system described above without departing from the scope of the present invention.

Figure 13:
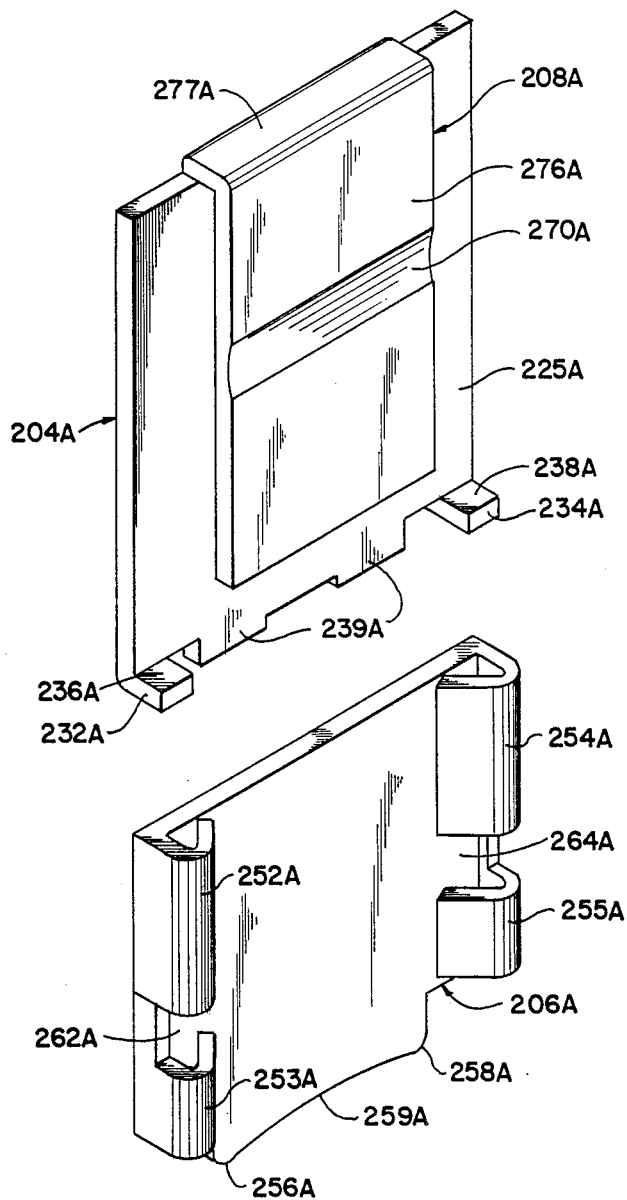
FIG. 13 is an exploded, isometric view of an alternative form of staple magazine positioner and guide plate and ram of the present invention.
Figure 14:
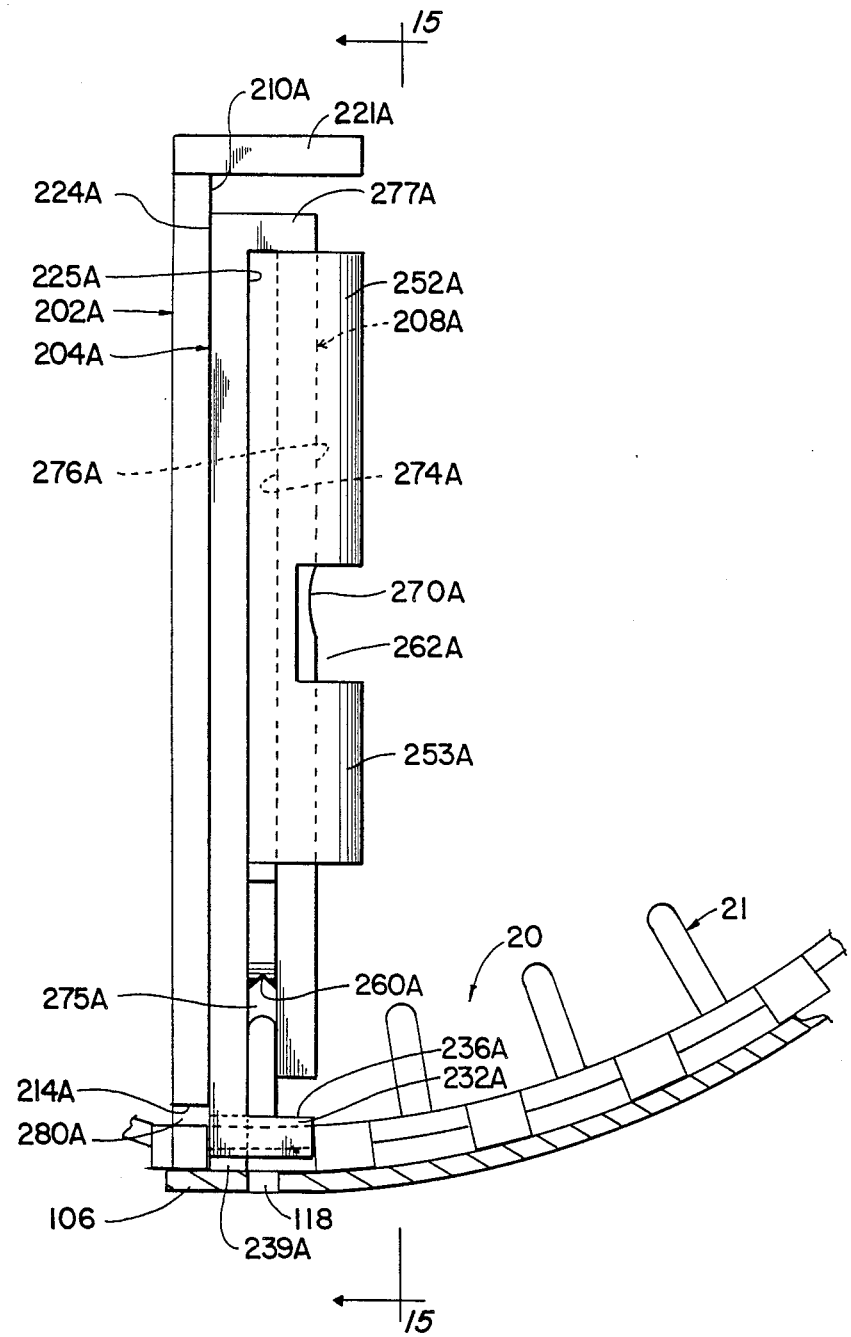
FIG. 14 a cross-sectional, side elevation view of the forward portion of the stapler employing an alternative form of bulkhead, staple magazine positioner, guide plate and ram.
Figure 15:
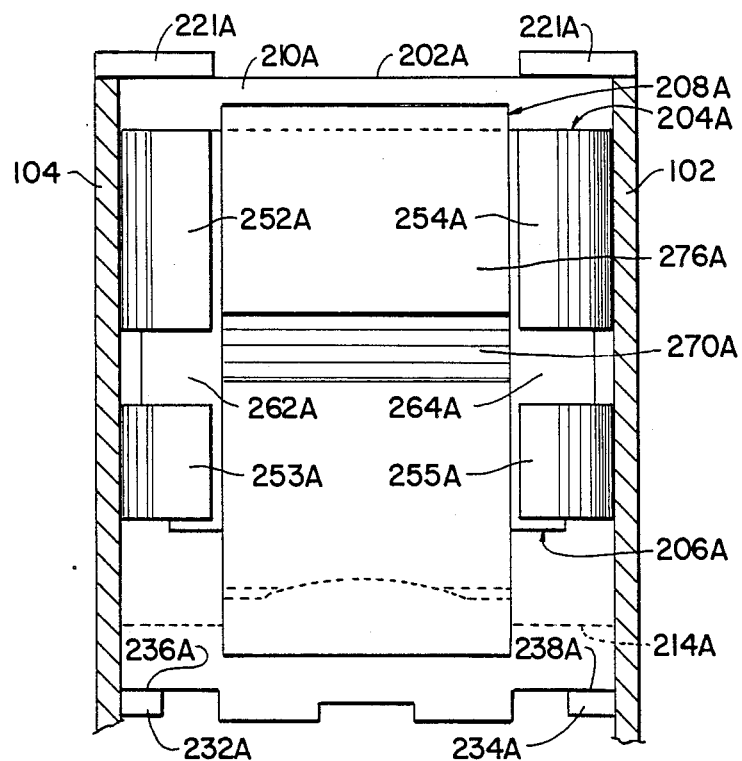
FIG. 15 is a partial, cross-sectional front elevation view taken along line 15-15 of FIG. 14, with the staple magazine and portions of the housing removed.

For example, the staple support and ram assembly 200 described above may be modified somewhat so as to take on the form shown in FIGS. 13-15.

More specifically, bulkhead 202A (FIGS. 14 and 15) is formed out of a flat plate having a planar inner surface 210A and a flat bottom surface 214A. Bulkhead 202A is disposed between the housing's opposing sidewalls 102 and 104 (FIG. 15) so as to form a barrier at the front end of housing 100. Bulkhead 202A is sized so that when its upper surface is flush with the tops of sidewalls 102 and 104, the bulkhead's bottom surface 214A will be spaced from the housing's bottom wall 106, whereby a magazine ejection slot 280A will be formed at the front end of the housing (FIG. 14). A pair of stops 221A are disposed about the corners where bulkhead 202A meets sidewalls 102 and 104, and stops 221A extend rearward therefrom.

Staple magazine positioner 204A and guide plate 208A (FIGS. 13-15) are formed out of a single piece of sheet metal which is bent into a generally u-shaped configuration whereby the body of guide plate 208A extends parallel to, but spaced from, the body of magazine positioner 204A. More specifically, magazine positioner 204A comprises a flat plate having a front side 224A and a rear side 225A (FIG. 14). Magazine positioner 204A has a pair of feet 232A and 234A extending perpendicularly away from the plate at its bottom end; feet 232A and 234A terminate in ram stop surfaces 236A and 238A or their upper sides, respectively. A pair of bottom extensions 239A extend down from the plate, below feet 232A and 234A.

Guide plate 208A comprises a flat plate having a front side 274A and a rear side 276A. A shallow surface groove 270A extends horizontally across the rear side 276A of guide plate 208A. Guide plate 208A is joined to staple magazine positioner 204A as shown, with guide plate 208A and magazine positioner 204A being separated by a gap 275A (FIG. 14) which extends between the rear surface 225A of magazine positioner 204A and the front surface 274A of guide plate 208A. It is to be appreciated that the complete assembly of staple magazine positioner 204A and guide plate 208A can be easily fabricated from a single piece of sheet metal.

Ram 206A is also intended to be fabricated from a single piece of sheet metal. Ram 206A comprises a flat plate which is provided with side flanges which are bent back so as to form side members 252A, 253A, 254A and 255A (FIG. 13). Slots 262A and 264A are formed between side members 252A and 253A and side members 254A and 255A, respectively. Slots 262A and 264A are aligned with one another and are analogous to the slots 262 and 264 formed in the aforementioned ram 206. The bottom end of ram 206A is provided with two lugs 256A and 258A which define a recessed, convexly curved portion 259A. A bottom surface groove 260A (FIG. 14) runs along the bottom of lugs 256A and 258A and curved portion 259A.

Bulkhead 202A, staple magazine positioner 204A, guide plate 208A and ram 206A are assembled and interact as follows. Ram 206A is slid into the gap 275A formed between staple magazine positioner 204A and guide plate 208A so that ram 206A makes a sliding fit between rear surface 225A of magazine positioner 204A and front surface 274A of guide plate 208A. Guide plate 208A is sized so that it will ride between the ram's opposing side members 252A and 254A and the opposing side members 253A and 255A. Staple magazine positioner 204A, guide plate 208A and ram 206A are also dimensioned such that when the top surface of ram 206A is in engagement with the portion of stock (indicated generally at 277A in FIGS. 13 and 14) which joins staple magazine positioner 204A and guide plate 208A together, surface groove 270A will be substantially aligned with slots 262A and 264A of ram 206A (FIG. 14). Furthermore, staple magazine positioner 204A, guide plate 208A and ram 206A are dimensioned such that when ram 206A is disposed between staple magazine positioner 206A, the ram's side members 252A, 253A, 254A and 255A will extend rearward significantly beyond rear surface 276A of guide plate 208A, and the ram's aligned slots 262A and 264A will have a substantially greater depth than the guide plate's surface groove 270A (FIG. 14). The assembled staple magazine positioner 204A, guide plate 208A and ram 206A are positioned inside housing 100 as shown in FIGS. 14 and 15 so that front surface 224A of staple magazine positioner 204A bears against bulkhead 202A, with staple magazine positioner 204A, guide plate 208A and ram 206A residing beneath stops 221A.

Operation of bulkhead 202A, staple magazine positioner 204A, guide plate 208A and ram 206A is analogous to the operation of the staple support and ram assembly 200 previously described, i.e., the tab 414 of ram driver plate 412 is positioned in surface groove 270A of guide plate 208A and slots 262A and 264A of ram 206A. When ram driver plate 412 is driven forwardly, e.g. under the influence of the aforementioned driver of Richards et al., ram 206A, guide plate 208A and, of course, the guide plate's attached staple magazine positioner 204A are all driven downward, until the staple magazine positioner's feet 232A and 234A enter the magazine's side pockets 52 and 54 and thereafter bottom on the housing's bottom surface 106, whereupon further downward movement of staple magazine positioner 204A and guide plate 208A is prohibited. At this point staple magazine positioner 204A and guide plate 208A will have slid along the leading and trailing edges of the staple 21 which is about to be deployed, thereby creating a constraining environment for the vertical staple movement which is about to occur.

Continued downward movement of ram driver plate 412 causes tab 414 to slip out of the guide plate's surface groove 270A, thereby decoupling guide plate 208A and staple magazine positioner 204A from tab 414. Ram 206A remains coupled to ram driver plate 412, however, by virtue of the fact that tab 414 remains engaged with slots 262A and 264A of ram 206A. Accordingly, ram 206A continues its downward movement under the influence of ram driver plate 412 so that staple 21 is engaged by ram 206A and driven from the stapler in the manner previously described. It is to be appreciated that as ram 206A is driven downward in the foregoing manner, staple magazine positioner 204A is retained in engagement with the housing's bottom surface 106 by virtue of the frictional contact existing between tab 414 of ram driver 412 and surface 276A of guide plate 208A. Downward movement of ram 206A is halted when the bottom surfaces of the ram's side members 253A and 255A engage ram stop surfaces 236A and 238A disposed on the staple magazine positioner's feet 232A and 234A.

Subsequently, when ram driver plate 412 returns upward, ram 206A will be pulled upward by virtue of the engagement between the ram driver plate's tab 414 and the ram's slot 262A and 264A. As ram 206A starts upward, guide plate 208A (and hence the attached staple magazine positioner 204A) will be pulled upward by virtue of the frictional contact between the withdrawing tab 414 and surface 276A of guide plate 208A. Staple magazine positioner 204A and guide plate 208A are dragged upward along with the retreating tab 414 of ram driver plate 412 (and also ram 206A, of course) until the top of magazine positioner 204A engages stops 221A which are fixed to the tops of bulkhead 202A and sidewalls 102 and 104, whereupon upward movement of magazine positioner 204A and guide plate 208A ceases. Tab 414 of ram driver plate 412 continues to move upward, however, sliding along the rear surface 276A of guide plate 208A and carrying ram 206A with it, until the top of the ram engages the stock 277A joining staple magazine positioner 204A and guide plate 208A, whereupon tab 414 reengages surface groove 270A of guide plate 208A and magazine positioner 204A, guide plate 208A, and ram 206A have all been moved back to their original starting positions.

Figure 16:
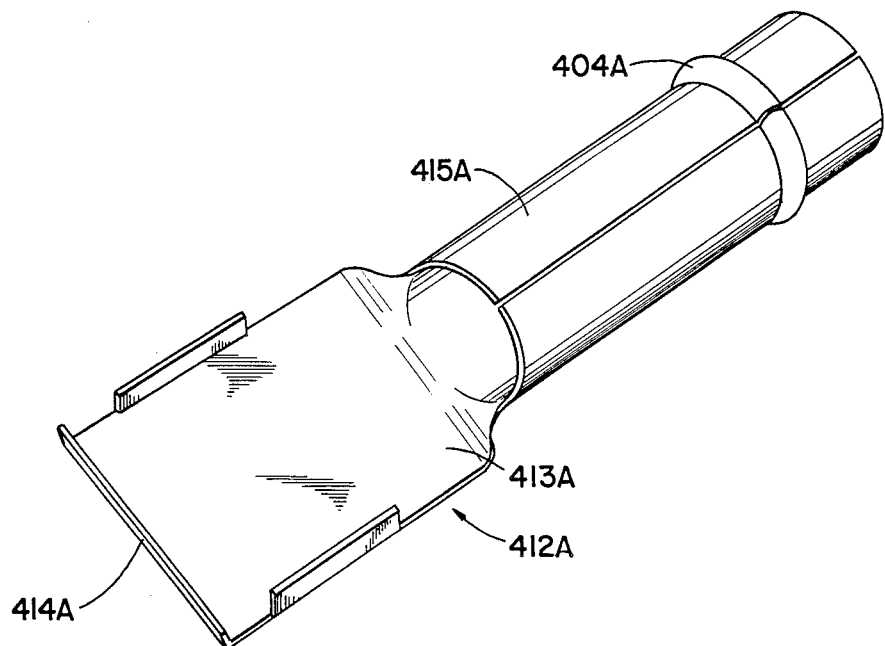
FIG. 16 is of an isometric view of an alternative form of driver plate.

Another contemplated variation is to replace the ram driver plate 412 and the stiffener plate 416 with an alternative driver plate 412A shown in FIG. 16. Driver plate 412A comprises a flat portion 413A which has a tab 414A set at its front end and a tubular portion 415A at its rear end. Tab 414A is adapted to engage slots 262 and 264 in ram 206 (or slots 262A and 264A in ram 206A)

and to engage surface groove 270 in guide plate 208 (or surface groove 270A in guide plate 208A). Tubular portion 415A replaces shaft 402 and drive flange 404 is replaced by a ring 404A. It will be appreciated that during operation of driver plate 412A, tubular portion 415A will remain substantially rigid and flat portion 413A will flex as the driver plate is driven toward the staple support and ram assembly 200. It will also be appreciated that driver plate 412A can be easily fabricated from a single piece of sheet metal stock.

Figure 17:
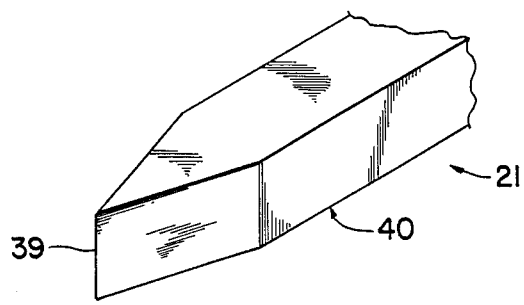
FIGS. 17 and 18 are isometric views of various staple embodiments.

Yet another contemplated modification involves the staples themselves. Looking next at FIG. 17, there is shown the end of one of the legs of a staple 21 of the sort disclosed in FIGS. 1–12. For convenience, the leg has been labelled as leg 40, although it will be appreciated that legs 38 and 40 are identical to one another and the leg could as easily be labelled leg 38 as leg 40. In any case, it will be noted that the leg has a generally rectangular cross-section near its tip, and the tip itself if formed by cutting away two sides of the leg so as to form a leading cutting edge 39.

Figure 18:
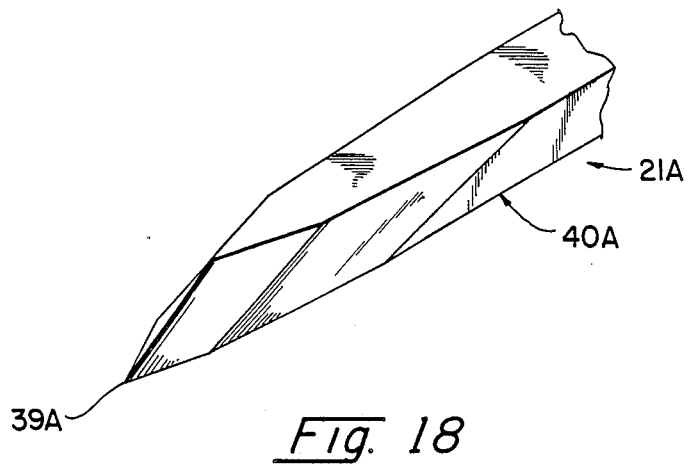

A modification of this design is shown in FIG. 18, wherein the leg 40A of staple 21A is cut away with a more complex arrangement so as to form a leading cutting tip 39A.

Since certain changes may be made in the present stapling system without departing from the scope of the invention herein involved, it is intended that all matter contained in the above description or shown in the accompanying drawing shall be interpreted in an illustrative and not in a limiting sense.

What is claimed is:

1. A surgical stapler for use with a staple magazine having a plurality of integrally-formed staples aligned in series, with each staple having two legs with ends that are adapted to pierce tissue, said stapler comprising:
  a first wall having a staple ejection slot;
  staple supporting means positioned adjacent said ejection slot for slidably supporting front and back surfaces of a leading staple in the staple magazine, said staple supporting means comprising a second wall extending at an angle to said first wall and a third wall spaced from and extending in parallel with said second wall, said staple supporting means comprising means for supporting said third wall for slidable movement so that when said third wall is slidably moved to a first position said second wall and said third wall confront and support the front and back surfaces of the leading staple, respectively;
  drive means for engaging the magazine and for urging the magazine to advance along said first wall so that the front surface of the leading staple in the magazine engages and is stopped by said second wall and for causing said third wall to move to said first position so that said third wall confronts the rear surface of the leading staple; and
  ram means slidably positioned adjacent said staple supporting means for (1) engaging the two legs of the leading staple, (2) driving the two legs downwardly along said second wall and said third wall and through said ejection slot into tissue engaged by said first wall, and (3) severing the leading staple from the magazine and driving the leading staple through said ejection slot into the tissue; and
  further wherein said drive means is coupled to said ram means.

2. A stapler according to claim 1 further wherein said drive means pulls said third wall and said ram means away from said staple ejection slot at the same time that said drive means urges the magazine along said first wall so as to cause the leading staple to engage said second wall.

3. A stapler according to claim 1 wherein said stapler further comprises a housing, said first wall comprises a bottom wall of said housing and said second wall comprises a front wall of said housing, and a staple magazine ejection slot is formed between said first wall and said second wall; and
  further wherein the staple magazine comprises a grid-like framework for supporting the plurality of staples, and said drive means is adapted to urge portions of the framework from which the staples have been sheared through said staple magazine ejection slot.

4. A stapler according to claim 3 further wherein:
  said ram means comprises a staple driving member slidably mounted between said second wall and said third wall for engaging and ejecting the leading staple from said housing;
  said drive means comprises an axially-movable shaft slidably received in said housing and having a flexible ram driving member affixed to said shaft for movement therewith, said ram driving member driably engages said staple driving member and said third wall so that (1) when said axially-movable shaft is moved in a first direction, said ram driving member drives said staple driving member toward said ejection slot and drives said third wall toward said first position, sand (2) when said axially-movable shaft is moved in a second direction, said ram driving member pulls said staple driving member away from said ejection slot and pulls said third wall away from said first position; and
  said drive means further comprises pawl means attached to said shaft and adapted to engage the staple magazine for driving the staple magazine along said first wall toward said second wall while said ram driving member simultaneously pulls said staple driving member away from said ejection slot and pulls said third wall away from said first position.

5. A stapler according to claim 4 further wherein:
  the staple magazine comprises a plurality of side pockets along outer edges of the magazine;
  said staple supporting means comprises magazine positioner means slidably mounted between said second wall and said staple driving member for engaging ones of the plurality of side pockets so as to prevent the staple magazine from moving when said staple driving member is driven toward said ejection slot, said magazine positioner means being adapted to engage the side pockets when said third wall is in said first position; and
  said stapler comprises a guide plate coupled to said magazine positioner means for slidable movement therewith, a front surface of said guide plate comprising said third wall and said guide plate having a back surface opposite said front surface.

6. A stapler according to claim 5, further wherein said staple driving member and said guide plate each comprise a notch for together receiving a forward end of said ram driving member, and wherein the notch in said staple driving member is deeper than the notch in said guide plate so that once said magazine positioner means engages the side pockets and said third wall is in said first position, additional movement of said exactly movable shaft in said first direction causes said ram driving member to slip out of the notch in said guide plate and slide along said back surface of said guide plate while said ram driving member remains engaged with the notch in said staple driving member and continues to drive said staple driving member toward said ejection slot.

7. A stapler according to claim 4 wherein said drive means comprises biasing means for urging said axially movable shaft in said second direction.

8. A stapler according to claim 1 wherein said drive means comprises a drive body for attaching said system to a staple driver.

9. A stapler according to claim 1 wherein said staple supporting means further comprises stop means for limiting the downward travel of said ram means.

10. A stapler according to claim 1 wherein said second and third walls are attached to one another.

11. A stapler according to claim 10 wherein the staple magazine comprises a plurality of side pockets along the outer edges of the magazine, and said second wall comprises magazine positioner means mounted on said second wall for engaging ones of the plurality of side pockets when said third wall is positioned in said first position so as to prevent the staple magazine from moving when said ram means engages the leading staple.

12. A multi-staple staple carrier strip formed from a sheet of a selected metal, said staple carrier strip comprising:
a pair of side frame members and a plurality of cross-frame members extending between and attached to said side frame members;
a plurality of staples each disposed between said side frame members and a pair of said cross-frame members; and
a plurality of tabs extending between and attached to said staples and said cross-frame members, whereby said staples are mounted in a fixed spatial relationship to said cross-frame members;
at least one of said side frame members cooperating with said cross-frame members to define a plurality of pocket-defining portions along said outer edges of said strip, said pocket-defining portions being sized to cooperate with associated portions of a staple driver used to deploy said staples from said staple carrier strip.

13. A staple carrier strip according to claim 18 wherein each of said side frame members cooperate with said cross-frame members to define a plurality of pocket-defining portions along said outer edges of said strip.

14. A staple carrier strip according to claim 12 wherein said staples have a body section and a pair of legs extending from opposite sides of said body section, said legs extending in a plane perpendicular to the plane of said frame so that said legs protrude from said frame.

15. A staple carrier strip according to claim 14 wherein each staple's body section extends parallel to said cross-frame members.

16. A staple carrier strip according to claim 15 wherein portions of said cross-frame members reside in a common plane.

17. A staple carrier strip according to claim 16 wherein each leg section is curved in a plane extending at a right angle to said common plane.

18. A staple carrier strip according to claim 17 wherein each leg section is circularly curved.

19. A staple carrier strip according to claim 15 wherein said pair of leg sections have pointed ends, and said pointed ends are disposed in diverging relation to one another.

20. A staple carrier strip according to claim 15 wherein each body section is disposed between two parallel cross-frame members and is attached to each of said two parallel cross-frame members by two mutually spaced tabs.

21. A staple carrier strip according to claim 15 wherein each body section is disposed between two parallel cross-frame members and is attached to one of said two cross-frame members by one of said tabs and to the other of said two cross-frame members by two of said tabs.

22. A staple carrier strip according to claim 15 wherein each body section is disposed between two parallel cross-frame members and is attached to each of said two cross-frame members by a single one of said tabs.

23. A staple carrier strip according to claim 15 wherein said tabs have a thickness less than the thickness of said cross-frame members and the thickness of said staples.

24. A staple carrier strip according to claim 12 wherein said tabs are preweakened adjacent said staples so as to facilitate separation of said staples from said staple carrier strip.

25. A staple carrier strip according to claim 24 wherein said tabs are prestressed adjacent said staples by formation of a microscopic step to facilitate separation of said staples from said staple carrier strip.

26. A staple carrier strip according to claim 12 wherein said cross-frame members are bent back upon themselves near their opposite ends so that said side frame members extend in cooperating relation with said cross-frame members.

27. A staple carrier strip according to claim 26 wherein portions of said cross-frame members lie in a different plane than side frame members.

28. A surgical stapler for use with a staple magazine having a plurality of integrally-formed staples aligned in series, with each staple having two legs with ends that are adapted to pierce tissue, said stapler comprising:
a first wall having a staple ejection slot;
staple supporting means positioned adjacent said ejection slot for slidably supporting front and back surfaces of a leading staple in the staple magazine, said staple supporting means comprising a second wall extending at an angle to said first wall and a third wall spaced from and extending in parallel with said second wall, said staple supporting means comprising means for supporting said third wall for slidable movement so that when said third wall is slidably moved to a first position wherein said third wall engages said leading staple, said second wall and said third wall engage and support the front and back surfaces of the leading staple, respectively;
drive means for engaging the magazine and for urging the magazine to advance along said first wall so that said front surface of the leading staple in the magazine engages and is stopped by said second wall and for causing said third wall to move to said first position so that said third wall engages the rear surface of the leading staple; and ram means slidably positioned adjacent said staple supporting means for (1) engaging the two legs of the leading staple, (2) driving the two legs downwardly along said second wall and said third wall and through said ejection slot into tissue engaged by said first wall, and (3) severing the leading staple from the magazine and driving the leading staple through said ejection slot into the tissue; and further wherein said drive means is coupled to said ram means.

29. A surgical stapling system for driving a staple into human or animal tissue comprising (a) a stapler and (b) a staple magazine having a plurality of integrally-formed staples aligned in series, with each staple having two legs with ends that are adapted to pierce said tissue, said stapler comprising:

a first wall having a staple ejection slot;

staple supporting means positioned adjacent said ejection slot for slidably supporting front and back surfaces of the leading staple in said magazine, said staple supporting means comprising a second wall extending at an angle to said first wall and a third wall spaced from and extending in parallel with said second wall, said staple supporting means comprising means for supporting said third wall for slidable movement so that when said third wall is slidably moved to a first position wherein said third wall engages said leading staple, said second wall and said third wall engage and support said front and back surfaces of said leading staple, respectively;

drive means engaging said magazine for urging said magazine to advance along said first wall so that said front surface of said leading staple in said magazine engage and is stopped by said second wall and for causing said third wall to move to said first position so that said third wall engages said rear surface of said leading staple; and ram means slidably positioned adjacent said staple supporting means for (1) engaging the two legs of said leading staple, (2) driving said two legs downwardly along said second wall and said third wall and through said ejection slot into tissue engaged by said first wall, and (3) severing said leading staple from said magazine and driving said leading staple through said ejection slot into said tissue; and further wherein said drive means is coupled to said ram means.

30. A system according to claim 29 further wherein said drive means pulls said third wall and said ram means away from said staple ejection slot at the same time that said drive means urges said magazine along said first wall so as to cause said leading staple to engage said second wall.

31. A system according to claim 29 wherein said stapler further comprises a housing, said first wall comprises a bottom wall of said housing and said second wall comprises a front wall of said housing, and a staple magazine ejection slot is formed between said first wall and said second wall; and further wherein said staple magazine comprises a grid-like framework for supporting said plurality of staples, and said drive means urges portions of said framework from which said staples have been sheared through said staple magazine ejection slot.

32. A system according to claim 31 wherein said grid-like framework is preweakened adjacent said staples to facilitate separation of said staples from said staple magazine.

33. A system according to claim 32 wherein said grid-like framework is prestressed adjacent said staples by formation fo a microscopic step to facilitate separation of said staples from said staple magazine.

34. A system according to claim 29 further wherein:

said ram means comprises a staple driving member slidably mounted between said second wall and said third wall for engaging and ejecting said leading staple from said housing;

said drive means comprises an axially-movable shaft slidably received in said housing and having a flexible ram driving member affixed to said shaft for movement therewith, said ram driving member drivably engages said staple driving member and said third wall so that (1) when said axially-movable shaft is moved in a first direction, said ram driving member drives said staple driving member toward said ejection slot and drives said third wall toward said first position, and (2) when said axially-movable shaft is moved in a second direction, said ram driving member pulls said staple driving member away from said ejection slot and pulls said third wall away from said first position; and said drive means further comprises pawl means attached to said shaft and engaging said staple magazine for driving said staple magazine along said first wall toward said second wall while said ram driving member simultaneously pulls said staple driving member away from said ejection slot and pulls said third wall away from said first position.

35. A system according to claim 34 further wherein:

said staple magazine comprises a plurality of side pockets along outer edges of said magazine;

said staple supporting means comprises magazine positioner means slidably mounted between said second wall and said staple driving member for engaging ones of said plurality of side pockets so as to prevent said staple magazine from moving when said staple driving member is driven toward said ejection slot, said magazine positioner means engaging said side pockets when said third wall is in said first position; and said stapler comprises a guide plate coupled to said magazine positioner means for slidable movement therewith, a front surface of said guide plate comprising said third wall and said guide plate having a back surface opposite said front surface.

36. A system according to claim 35 further wherein said staple driving member and said guide plate each comprise a notch for together receiving a forward end of said ram driving member, and wherein the notch in said staple driving member is deeper than the notch in said guide plate so that once said magazine positioner means engages said side pockets and said third wall is in said first position, additional movement of said axially movable shaft in said first direction causes said ram driving member to slip out of the notch in said guide plate and slide along said back surface of said guide plate while said ram driving member remains engaged with the notch in said staple driving member and continues to drive said staple driving member toward said ejection slot.

37. A system according to claim 20 wherein said drive means comprises biasing means for urging said axially movable shaft in said second direction.

38. A system according to claim 29 wherein said drive means comprises a drive body for attaching said system to a staple driver.

39. A system according to claim 29 wherein said staple supporting means further comprises stop means for limiting the downward travel of said ram means.

40. A system according to claim 29 wherein said second and third walls are attached to one another.

41. A system according to claim 40 wherein said staple magazine comprises a plurality of side pockets along the outer edges of said magazine, and said second wall comprises magazine positioner means mounted on said second wall for engaging ones of said plurality of side pockets when said third wall is positioned in said first position so as to prevent said staple magazine from moving when ram means engages said leading staple.

42. A surgical stapling system for driving a staple into human or animal tissue comprising (a) a stapler and (b) a staple magazine having a plurality of integrally-formed staples aligned in series, with each staple having two legs with ends that are adapted to pierce said tissue, said stapler comprising:
- a first wall having a staple ejection slot;
- staple supporting means positioned adjacent said ejection slot for slidably supporting front and back surfaces of the leading staple in said magazine, said staple supporting means comprising a second wall extending at an angle to said first wall and a third wall spaced from and extending in parallel with said second wall, said staple supporting means comprising means for supporting said third wall for slidable movement so that when said third wall is slidably moved to a first position said second wall and said third wall confront and support said front and back surfaces of said leading staple, respectively;
- drive means engaging said magazine for urging said magazine to advance along said first wall so that said front surface of said leading staple in said magazine engages and is stopped by said second wall and for causing said third wall to move to said first position so that said third wall confronts said rear surface of said leading staple; and
- ram means slidably positioned adjacent said staple supporting means for (1) engaging the two legs of said leading staple, (2) driving said two legs downwardly along said second wall and said third wall and through said ejection slot into tissue engaged by said first wall, and (3) severing said leading staple from said magazine and driving said leading staple through said ejection slot into said tissue; and
- further wherein said drive means is coupled to said ram means.

43. A system according to claim 42 further wherein said drive means pulls said third wall and said ram means away from said staple ejection slot at the same time that said drive means urges said magazine along said first wall so as to cause said leading staple to engage said second wall.

44. A system according to claim 42 wherein said stapler comprises a housing, said first wall comprises a bottom wall of said housing and said second wall comprises a front wall of said housing, and a staple magazine ejection slot is formed between said first wall and said second wall; and
further wherein said staple magazine comprises a grid-like framework for supporting said plurality of staples, and said drive means urges portions of said framework from which said staples have been sheared through said staple magazine ejection slot.

45. A system according to claim 44 wherein said grid-like framework is preweakened adjacent said staples to facilitate separation of said staples from said staple magazine.

46. A system according to claim 45 wherein said grid-like framework is prestressed adjacent said staples by formation of a microscopic step to facilitate separation of said staples from said staple magazine.

47. A system according to claim 44 further wherein:
said ram means comprises a staple driving member slidably mounted between said second wall and said third wall for engaging and ejecting said leading staple from said housing;
said drive means comprises an axially-movable shaft slidably received in said housing and having a flexible ram driving member affixed to said shaft for movement therewith, said ram driving member drivably engages said staple driving member and said third wall so that (1) when said axially-movable shaft is moved in a first direction, said ram driving member drives said staple driving member toward said ejection slot and drives said third wall toward said first position, and (2) when said axially-movable shaft is moved in a second direction, said ram driving member pulls said staple driving member away from said ejection slot and pulls said third wall away from said first position; and
said drive means further comprises pawl means attached to said shaft and engaging said staple magazine for driving said staple magazine along said first wall toward said second wall while said ram driving member simultaneously pulls said staple driving member away from said ejection slot and pulls said third wall away from said first position.

48. A system according to claim 44 further wherein:
said staple magazine comprises a plurality of pocket-defining members defining a plurality of side pockets along outer edges of said magazine;
said staple supporting means comprises magazine positioner means slidably mounted between said second wall and said staple driving member for insertion into ones of said plurality of side pockets so as to prevent said staple magazine from moving when said staple driving member is driven toward said ejection slot, said magazine positioner means engaging said pocket-defining members when said third wall is in said first position; and
said stapler comprises a guide plate coupled to said magazine positioner means for slidable movement therewith, a front surface of said guide plate comprising said third wall and said guide plate having a back surface opposite said front surface.

49. A system according to claim 48 wherein said staple magazine comprises a multi-staple staple carrier strip formed from a sheet of a selected metal, said staple carrier strip comprising:
a pair of side frame members and a plurality of cross-frame members extending between and attached to said side frame members;
a plurality of staples each disposed between said side frame members and a pair of cross-frame members; and
a plurality of tabs extending between and attached to said staples and said cross-frame members, whereby said staples are mounted in a fixed spatial relationship to said cross-frame members;

and further wherein said plurality of side pockets are formed at least in part by said side frame members.

50. A system according to claim 49 wherein said side frame members each cooperate with said cross-frame members to define a plurality of pocket-defining portions along said outer edges of said magazine.

51. A system according to claim 49 wherein said staple ejection slot is sized so as to support the tabs associated with said leading staple when said leading staple is severed from said staple magazine and driven through said ejection slot.

52. A system according to claim 49 wherein said cross-frame members are bent back upon themselves adjacent said side frame members.

53. A system according to claim 48 further wherein said staple driving member and said guide plate each comprise a notch for together receiving a forward end of said ram driving member, and wherein the notch in said staple driving member is deeper than the notch in said guide plate so that once said magazine positioner means is inserted into said side pockets and said third wall is in said first position, additional movement of said axially movable shaft in said first direction causes said ram driving member to slip out of the notch in said guide plate and slide along said back surface of said guide plate while said ram driving member remains engaged with the notch in said staple driving member and continues to drive said staple driving member toward said ejection slot.

54. A system according to claim 47 wherein said drive means comprises biasing means for urging said axially movable shaft in said second direction.

55. A system according to claim 42 wherein said drive means comprises a drive body for attaching said system to a staple driver.

56. A system according to claim 42 wherein said staple supporting means further comprises stop means for limiting the downward travel of said ram means.

57. A system according to claim 42 wherein said second and third walls are attached to one another.

58. A system according to claim 57 wherein said staple magazine comprises a plurality of pocket-defining members defining a plurality of side pockets along the outer edges of said magazine, and second wall comprises magazine positioner means mounted on said second wall for insertion into ones of said plurality of side pockets when said third wall is positioned in said first position so as to prevent said staple magazine from moving when ram means engages said leading staple.

59. A system according to claim 42 wherein said second wall is fixed in position relative to said first wall.

60. A system according to claim 42 wherein said staple supporting means further comprises means for supporting said second wall for slidable movement towards and away from said first wall.

61. A system according to claim 60 wherein said staple supporting means further comprises a fourth wall, and said second wall is adapted to slide along said fourth wall as said second wall moves towards and away from said first wall.

62. A system according to claim 60 wherein said second wall and said third wall are attached to one another.

63. A system according to claim 42 wherein
said staple magazine comprises a plurality of pocket-defining members defining a plurality of side pockets along outer edges of said magazine; and
said staple supporting means comprises magazine positioner means for insertion into ones of said plurality of side pockets so as to prevent said staple magazine from moving when said ram means is driving said leading staple through said ejection slot.

64. A system according to claim 63 wherein said staple supporting means further comprises means for supporting said second wall for slidable movement towards and away from said first wall, and further wherein said magazine positioner means are attached to said second wall.

* * * * *